US00PP15577P3

(12) United States Plant Patent
Oud

(10) Patent No.: US PP15,577 P3
(45) Date of Patent: Feb. 22, 2005

(54) ***OSTEOSPERMUM* PLANT NAMED 'OSJOTIS'**

(50) Latin Name: *Osteospermum ecklonis*
Varietal Denomination: Osjotis

(75) Inventor: Johannes Simon Nicolaas Oud, Bovenkarspel (NL)

(73) Assignee: Syngenta Seeds B.V., Enkhuizen (NL)

( * ) Notice: Subject to any disclaimer, the term of this patent is extended or adjusted under 35 U.S.C. 154(b) by 84 days.

(21) Appl. No.: 10/342,638

(22) Filed: Jan. 15, 2003

(65) Prior Publication Data

US 2004/0139522 P1 Jul. 15, 2004

(51) Int. Cl.[7] ..... A01H 5/00
(52) U.S. Cl. ..... Plt./360
(58) Field of Search ..... Plt./360

*Primary Examiner*—Kent Bell
*Assistant Examiner*—Louanne Krawczewicz Myers
(74) *Attorney, Agent, or Firm*—Edouard G. Lebel

(57) ABSTRACT

A new *Osteospermum* plant particularly distinguished by its very compact round plant habit, early flowering with light purple colored ray florets and blue colored disc florets.

1 Drawing Sheet

Latin name: *Osteospermum ecklonis.*
Varietal denomination: Osjotis.

BACKGROUND OF THE NEW PLANT

The present invention relates to a new and distinct cultivar of *Osteospermum* plant, botantially known as *Osteospermum ecklonis.* The new *Osteospermum* is propagated by cuttings resulting from a cross of a proprietary *Osteospermum ecklonis* seedling selection as the male, or pollen, parent identified as code number 'C274' with a proprietary *Osteospermum ecklonis* selection identified as code number 'C298' as the female, or seed, parent. 'C274' has a plant height of 30 cm and a plant width of 20 cm. 'C298' has a plant height of 18 cm and a plant width of 12 cm.

The new *Osteospermum* was discovered and selected as a single flowering plant within the progeny of the stated cross grown in Enkhuizen, Netherlands, in 1998. Neither 'C274' nor 'C298' has been patented. The new *Osteospermum* plant has been repeatably asexually reproduced by cuttings in Enkhuizen, Netherlands over a period of 3 years. It has been found to retain its distinctive characteristics through successive propagations, and this novelty appears to be firmly fixed.

DESCRIPTION OF THE DRAWING

This new *Osteospermum* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Osteospermum* plant. The data which defines these characteristics were collected from asexual reproductions carried out in Enkhuizen, Netherlands. The plant history was taken on 15 weeks old plants. Color references are primarily to The R.H.S. Colour Chart of The Royal Horticultural Society of London. The instant plant was grown indoors in a 10.5 cm container.

Comparison between the new cultivar 'Osjotis' and a similar cultivar

| | 'Osjotis' | 'Sea side' (U.S. Plant Pat. No. 10,782) |
|---|---|---|
| Plant height | 20 cm | 30 cm |
| Plant width | 15 cm | 20 cm |
| Flowering response | | Opening of first flower one one week later |

The Plant

Classification — botanical: *Osteospermum ecklonis.*

Parentage

Female parent: A seedling named 'C298' is one of our seedlings from our C-generation of plants bred in 1998.
Male parent: A seedling named 'C274' is one of our seedlings from our C-generation of plants bred in 1998.

Plant Description

Growth habit: Round, compact.
Plant height: 20 cm.
Speading area of plant: 15 cm.
Strength: Moderate growth.
Branching character: Freely branching, 20 lateral branches without pinching.
Blooming period: From May until October.

The Stem

Length: 10 cm.
Diameter: 4 mm.
Internode length: 8 mm.
Texture: Glabrous.
Color: RHS 137C.

The Foliage

Shape: Single leaves, alternate and elliptic, apex: broadly acute base: attenuate, margin: irregular serration.
Number of leaves per lateral branch: 13.
Texture: Glabrous, leathery.
Leaf:
*Color — upper side.*—RHS 137B.
*Color — under side.*—RHS 137D.
*Length.*—Young 30 mm, mature 70 mm.
*Width.*—Young 10 mm, mature 40 mm.
*Petiole.*—Absent.

The Inflorescence

Number of inflorescences per mature plant: 100.
Inflorescence bud:
*Form.*—Ovoid.
*Length.*—20 mm.
*Width.*—12 mm.
*Color.*—RHS N79D.
Inflorescence lastingness of the plant: Around 5 days depending on temperature.
Inflorescence:
*Diameter.*—63 mm.
*Disc diameter.*—9 mm.
Inflorescence depth: 12 mm.
Fragrance: No fragrance.
Disc florets:
*Shape.*—Tubular, elongated.
*Apex.*—Five pointed.
*Length.*—7 mm.
*Width.*—1 mm.
*Number of disc florets per inflorescence.*—60.
*Color.*—RHS 99B.
Ray florets:
*Length.*—27 mm.
*Width.*—7 mm.
*Arrangement.*—Capitulum with one series of ray florets.
*Color.*—Upper surface: RHS 77C. Lower surface: RHS N79D.
*Number of ray florets.*—20.
*Shape.*—Apex: Rounded. Base: Acute. Margin: Entire.
*Texture.*—Satiny.
Peduncles:
*Length.*—8 cm.
*Texture.*—Sturdy, tiny hairs.
*Color.*—RHS 137C.
*Diameter.*—1.5 mm.
*Shape.*—Round.
Phyllaries:
*Texture.*—Rough, tiny hairs.
*Number of phyllaries.*—20.
*Length.*—10 mm.
*Margin.*—Entire.
*Width.*—1 mm.
*Apex.*—Acute.
*Shape.*—Ligulate.
*Color.*—RHS 137C both sides.

Reproductive Organs

Androecium:
*Appearance.*—Present on disc florets only.
*Shape.*—Oblong, five stamen fused to one.
*Length.*—2 mm.
*Width.*—1 mm.
*Pollen color.*—RHS 25A.
*Total no. of anthers.*—60.
Gynoecium:
*Appearance.*—Present on both ray and disc florets.
*Pistil number.*—One pistil per ray or disc floret.
*Pistil length.*—4 mm.
*Stigma color.*—RHS 77A.
*Stigma shape.*—Bipartite.

Seed Development

Seed development has been observed on plants of the new *Osteospermum*.

Amount of seeds produced: Moderate.
Seed length: 6 mm.
Diameter: 3 mm.
Color: RHS 200A.
Shape: Elliptic.

Disease Resistance

Under commercial conditions, plants of the new *Osteospermum* are resistant to fungal pathogens common to *Osteospermum*.

What is claimed is:

1. A new and distinct variety of *Osteospermum* plant, substantially as illustrated and described herein.

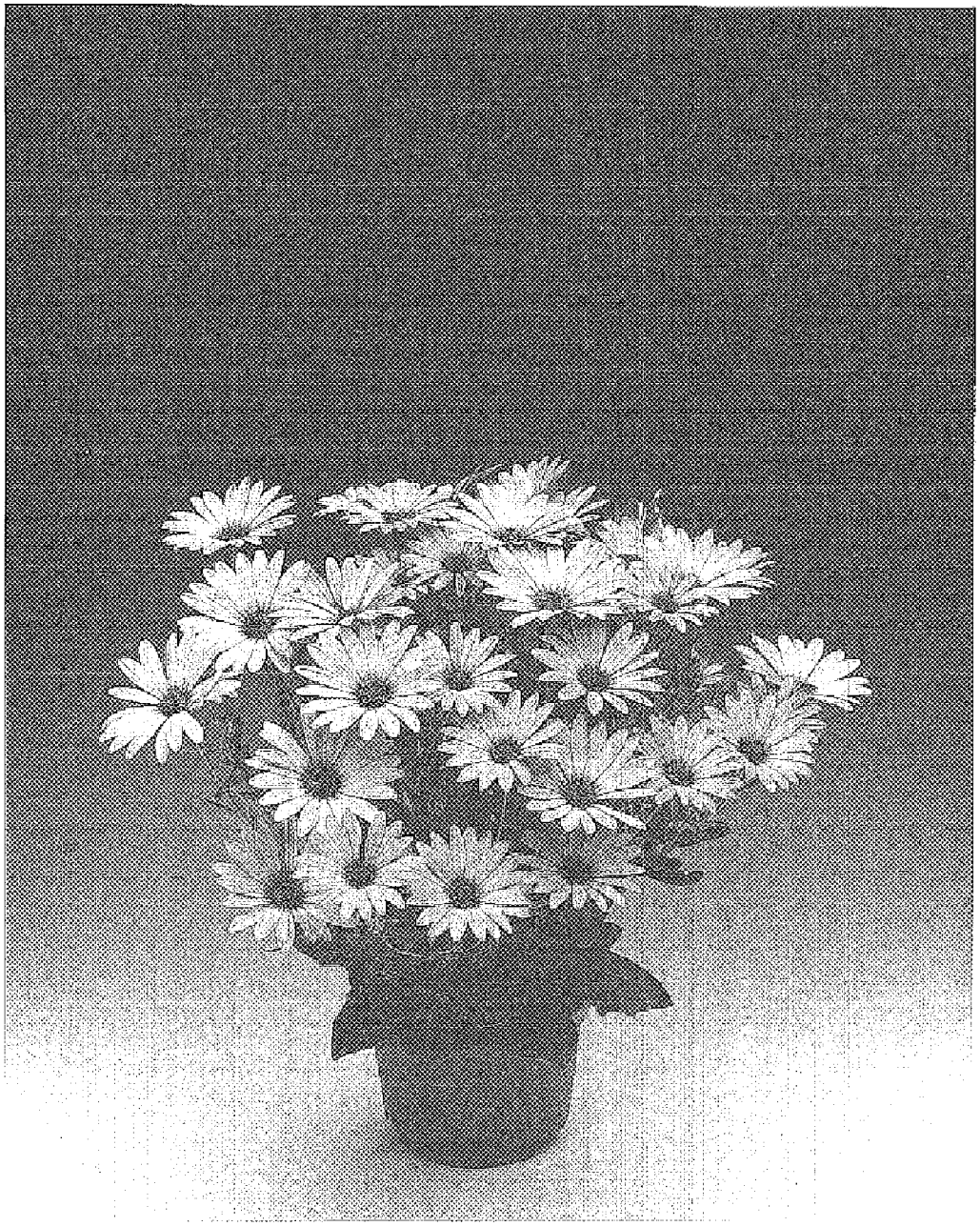

* * * * *